(12) United States Patent
Little

(10) Patent No.: US 7,996,688 B2
(45) Date of Patent: Aug. 9, 2011

(54) ULTRASOUND SYSTEM POWER MANAGEMENT

(75) Inventor: Blake W. Little, Bothell, WA (US)

(73) Assignee: SonoSite, Inc., Bothell, WA (US)

( * ) Notice: Subject to any disclaimer, the term of this patent is extended or adjusted under 35 U.S.C. 154(b) by 2104 days.

(21) Appl. No.: 10/924,390

(22) Filed: Aug. 24, 2004

(65) Prior Publication Data

US 2006/0058652 A1    Mar. 16, 2006

(51) Int. Cl.
| G06F 1/00 | (2006.01) |
| G06F 1/26 | (2006.01) |
| G06F 1/32 | (2006.01) |
| G01B 7/14 | (2006.01) |
| G01B 17/02 | (2006.01) |
| A61B 5/05 | (2006.01) |

(52) U.S. Cl. ........ 713/300; 713/320; 713/323; 702/159; 702/171; 128/916; 600/407

(58) Field of Classification Search .................. 713/300, 713/320, 323; 702/159, 171; 128/916; 600/407
See application file for complete search history.

(56) References Cited

U.S. PATENT DOCUMENTS

| 5,482,046 | A | 1/1996 | Deitrich |
| 5,722,412 | A | 3/1998 | Pflugrath et al. |
| 6,471,651 | B1 | 10/2002 | Hwang et al. |
| 6,527,721 | B1 * | 3/2003 | Wittrock et al. ............. 600/446 |
| 6,542,846 | B1 | 4/2003 | Miller et al. |
| 6,592,521 | B1 | 7/2003 | Urbano et al. |
| 7,338,446 | B2 * | 3/2008 | MacDonald et al. ......... 600/437 |
| 2006/0058652 | A1 * | 3/2006 | Little ............................ 600/437 |

FOREIGN PATENT DOCUMENTS

| JP | 200007062 | 3/2000 |
| JP | 2004159812 | 11/2002 |
| JP | 2003175035 | 6/2003 |

OTHER PUBLICATIONS

International Search Report and Written Opinion issued for PCT/US2005/030129 dated Dec. 6, 2005.

* cited by examiner

*Primary Examiner* — Ji H Bae
(74) *Attorney, Agent, or Firm* — Perkins Coie LLP

(57) ABSTRACT

Disclosed are systems and methods which power-down (reduce power to or deactivate) circuits in an ultrasound system during periods in which an acoustic signal is not being acquired, although image processing and other system functions are continued normally. Such circuits may be powered-down between each of a series of acoustic signal acquire operations, such as between acoustic signal scan lines and/or between acoustic signal scan frames. The circuitry which is powered-down between scan lines and scan frames may not be the same, although some circuitry may be common to both. Embodiments may further operate to adjust the acoustic signal dead time circuitry power-down cycle, such as by adjusting acoustic signal frame rates. Power-down techniques may be utilized in addressing power issues and/or in controlling thermal aspects of the operation of an ultrasound diagnostic system.

63 Claims, 1 Drawing Sheet

ULTRASOUND SYSTEM POWER MANAGEMENT

CROSS-REFERENCE TO RELATED APPLICATIONS

The present application is related to U.S. patent application Ser. No. 10/925,114filed Aug. 24, 2004, entitled "ULTRASONIC TRANSDUCER HAVING A THIN WIRE INTERFACE," and U.S. patent application Ser. No. 10/847,643, filed May 17, 2004, entitled "PROCESSING OF MEDICAL SIGNALS," the disclosures of which are incorporated herein by reference.

TECHNICAL FIELD

The invention is related to techniques for conserving power and, more particularly, to ultrasound system power conservation.

BACKGROUND OF THE INVENTION

In recent years advancements have been made in moving away from the well known large cart based ultrasonic diagnostic systems. Although complex cart based ultrasonic instruments generally provide excellent image quality and a number of features, such as B mode, color Doppler imaging, three-dimensional display, etcetera, the systems are typically very costly, quite heavy (e.g., weighing on the order of several hundred pounds), and allow for only limited portability (e.g., rolling of a supporting cart over smooth surfaces, as well as being limited to where there are house electrical outlets). However, the portable ultrasonic diagnostic systems of more recent development have addressed cost and portability issues while still providing numerous advanced features, such as B mode, color Doppler imaging, and three-dimensional display while providing excellent image quality. Some examples of portable ultrasonic diagnostic systems are provided in U.S. Pat. No. 5,722,412 entitled "Hand Held Ultrasonic Diagnostic Instrument" and U.S. Pat. No. 6,471,651 entitled "Low Power Portable Ultrasonic Diagnostic Instrument," the disclosures of which are incorporated herein by reference.

Operation of portable ultrasonic diagnostic systems has not, however, been without difficulty. For example, in order to provide truly portable systems, battery technology has been implemented with respect to many portable ultrasonic diagnostic systems. Although providing increased freedom of movement (e.g., not requiring there to be house electrical outlets where an ultrasonic procedure is performed and not being encumbered with power cables) such battery technologies introduce the issue of a limited power capacity. Accordingly, various power conservation techniques have been implemented with respect to portable ultrasonic diagnostic systems, such as placing the instrument in "sleep" mode when user input has not been detected for a predetermined amount of time. The above referenced United States patent entitled "Low Power Portable Ultrasonic Diagnostic Instrument" provides an example of prior attempts to conserve power with respect to a portable ultrasonic diagnostic system. Although many prior art systems provide a useful level of power management, there is a need in the art to further improve power management and optimize the conservation of power with respect to portable ultrasonic diagnostic systems.

BRIEF SUMMARY OF THE INVENTION

The present invention is directed to systems and methods which power-down (reduce power to or deactivate) circuits in an acoustic signal path during periods in which an acoustic signal is not being acquired by a portable ultrasonic diagnostic system, although image processing and other system functions may be continued normally. According to preferred embodiments, acoustic signal path circuits are powered-down between each of a series of acoustic signal acquire operations, such as between acoustic signal scan lines, between groups of scan lines, and/or between acoustic signal scan frames. By applying appropriate timing techniques, such acoustic signal path circuits may be again powered-up just prior to acoustic signal acquire operations, such as to transmit an acoustic pulse and/or receive a return echo, thereby minimizing the time such circuits are energized without otherwise affecting the operation of the portable ultrasonic diagnostic system.

Embodiments of the present invention operate to power-down particular acoustic signal path circuitry during acoustic signal "dead" time between acoustic signal line acquisition. For example, as a previous acoustic signal line is being processed, while circuitry such as beam formers are being configured for a next acoustic signal line acquisition, etcetera, circuitry such as transmit amplifiers, receive buffers, transmit/receive switches, diplexers, analog to digital (A/D) converters, digital signal processors (DSPs), and/or the like which are used in the acoustic signal path may be powered-down according to the present invention.

Similarly, embodiments of the present invention operate to power-down particular acoustic signal path circuitry during acoustic signal dead time between acoustic signal frames. For example, a plurality of the above mentioned acoustic signal lines, or a frame, may be utilized in providing an ultrasonic image. In the time between when a last acoustic signal line has been acquired for a previous frame and a first acoustic signal line is to be acquired for a next frame, circuitry such as transmit amplifiers, receive buffers, transmit/receive switches, diplexers, A/D converters, DSPs, and/or the like which are used in the acoustic signal path may be powered-down according to the present invention.

According to embodiments of the invention, the circuitry which is powered-down between lines and frames is not the same, although some circuitry is common to both. For example, it is expected that the acoustic signal dead time between acoustic signal frames will often be greater than the acoustic signal dead time between acoustic signal lines due to the increased processing burden associated with forming and displaying the resulting image. Accordingly, circuitry powered-down between acoustic signal frames according to embodiments of the present invention may include circuitry, in addition to the circuitry powered-down between acoustic signal lines, which requires a longer time to return to steady-state operation after power-up.

In order to further conserve power, embodiments of the present invention operate to adjust the acoustic signal dead time circuitry power-down cycle, such as by adjusting acoustic signal frame rates. For example, by determining a particular scan mode that the portable ultrasonic diagnostic system has been placed in, the acoustic signal frame rate may be adjusted to provide an optimized acoustic signal dead time circuitry power-down cycle, perhaps facilitating the powering-down of additional circuitry due to the length of the power-down cycle, without compromising the image quality expected in that mode of operation. Additionally or alternatively, by determining that the scanned image remains substantially unchanged, such as over a period of a predetermined number of frames, the acoustic signal frame rate may be adjusted to provide an increased acoustic signal dead time circuitry power-down cycle, thereby reducing power consumption, without compromising image quality (e.g., the frame rate is again increased to its original rate when the scanned image is changed) or otherwise affecting system operation.

Embodiments of the present invention implement the foregoing power-down techniques in various combinations, including combinations of the foregoing techniques as well as combinations of one or more of the foregoing techniques with other power management techniques. For example, power-down cycles may be implemented between acoustic signal lines and/or acoustic signal frames and an additional power management technique may be implemented wherein portable ultrasound diagnostic system circuitry not necessary for a currently selected mode of operation may be powered-down throughout operation of that mode. Similarly, power-down cycles may be implemented between acoustic signal lines and/or acoustic signal frames and an additional power management technique may be implemented wherein portable ultrasound diagnostic system circuitry not necessary for a currently selected component or accessory may be powered-down throughout use of that component or accessory.

Application of the foregoing power-down techniques of the present invention is not limited to addressing power issues. For example, embodiments of the present invention may be utilized in controlling thermal aspects of the operation of a portable ultrasound diagnostic system. Specifically, as portable ultrasonic diagnostic systems continue to be reduced in size and/or to include additional features, the density of the electronics therein increases, which may lead to issues in dissipating heat which results from their operation. However, embodiments of the present invention may be implemented to power-down circuitry, thereby decreasing the thermal output, without undesirably affecting operation of the portable ultrasonic diagnostic system. Moreover, if an excessive thermal condition is detected, such as through use of a thermister or other temperature detection apparatus, the foregoing technique of adjusting the acoustic signal dead time circuitry power-down cycle, such as by adjusting acoustic signal frame rates, may be invoked in order to allow thermal energy to dissipate. Such a technique may result in other than desired performance by the portable ultrasonic diagnostic system during such times, however such decreased performance is offset by the continued ability for the system to operate.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated that the conception and specific embodiment disclosed may be readily utilized as a basis for modifying or designing other structures for carrying out the same purposes of the present invention. It should also be realized that such equivalent constructions do not depart from the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWING

For a more complete understanding of the present invention, reference is now made to the following descriptions taken in conjunction with the accompanying drawing, in which.

DETAILED DESCRIPTION OF THE INVENTION

Figure 1:
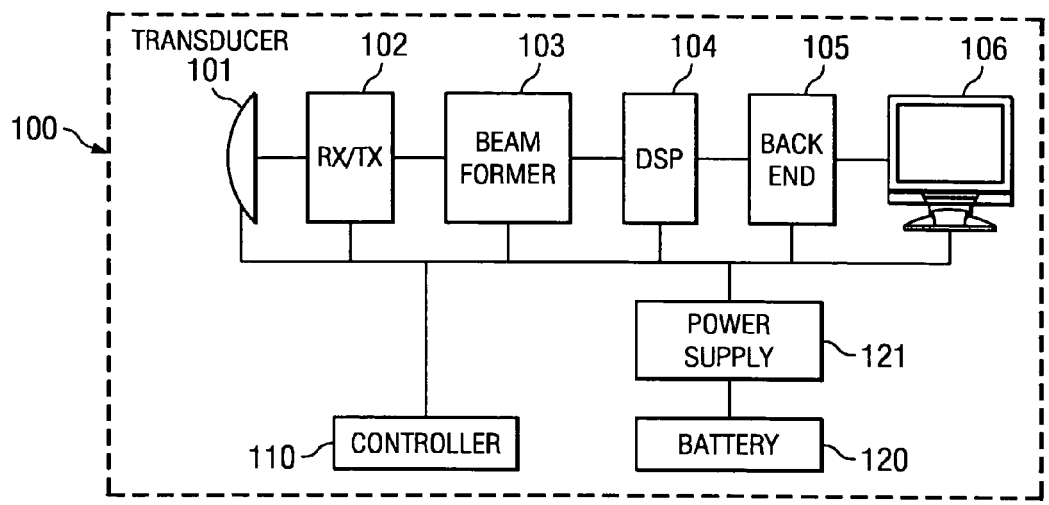
FIG. 1 shows a high level block diagram of an ultrasonic diagnostic system adapted according to an embodiment of the present invention.

Directing attention to FIG. 1, a high level block diagram of an ultrasonic diagnostic system adapted according to an embodiment of the present invention is shown as system 100. System 100 displays signals captured by transducer 101 (e.g., an array transducer) as images on monitor 106 (e.g., a cathode ray tube (CRT), liquid crystal display (LCD), gas plasma display, etcetera). The illustrated embodiment of system 100 includes 4 functional blocks, such as may comprise application specific integrated circuits (ASICs) between transducer 101 and monitor 106. Specifically, the embodiment of FIG. 1 includes transmit/receive module 102 which is connected to the elements of transducer 101, beamformer module 103 which may perform and control transmit and receive beamforming, digital signal processing (DSP) module 104 which may provide processing of the ultrasound signals such as filtering, and back end module 105 which may receive processed ultrasound signals and produce ultrasound image data for storage, analysis, display, etcetera.

Controller 110, shown coupled to transducer 101, transmit/receive module 102, beamformer module 103, DSP module 104, back end module 105, and monitor 106, provides control signals to one or more of the foregoing in implementing power management techniques of the present invention. Additionally, controller 110 may obtain information from one or more of the foregoing modules. For example, controller 110 may obtain temperature information from transducer 101 or operational mode information from back end module 105 for implementing power control techniques of the present invention by providing control signals to transmit/receive module 102, beamformer module 103, and/or DSP module 104, as will be better understood from the discussion which follows. Additionally, controller 110, which is in communication with battery 120, may obtain status information therefrom in order to invoke power control techniques appropriate to the condition of battery 120.

Controller 110 of a preferred embodiment comprises a processor having memory storing instructions operable upon the processor for defining operation as described herein. For example, controller 110 may comprise a central processing unit (CPU) in communication with random access memory (RAM) and/or read only memory (ROM) having one or more input/output interfaces, such as a control bus, inter-integrated circuit bus, etcetera, useful for communicating with and/or controlling other circuitry of system 100. Embodiments of the present invention may implement controller 110, or portions thereof, in an ASIC architecture.

Battery 120 comprises a portable power source adapted to provide energy to the components of system 100, such as through power supply 121, without the application of external power. For example, battery 120 may comprise lithium-ion, nickel-cadmium, lead acid, gel cell, or other battery technology, whether rechargeable or single use or may utilize a fuel cell. Power supply 121, coupled to battery 120 in the illustrated embodiment, may comprise power supply circuitry, such as may be coupled to house line current, useful in recharging battery cells thereof and/or for powering the system 100 in operation.

The foregoing exemplary embodiment of system 100 provides a configuration operable to provide a portable ultrasonic diagnostic system. Although the concepts of the present invention are particularly useful with respect to conserving power for use with respect to a portable ultrasonic diagnostic system, it should be appreciated that these concepts are not limited to application with respect to portable systems. Accordingly, embodiments of the present invention may be implemented with respect to a variety of system configurations, including cart based ultrasonic diagnostic systems.

Figure 2:
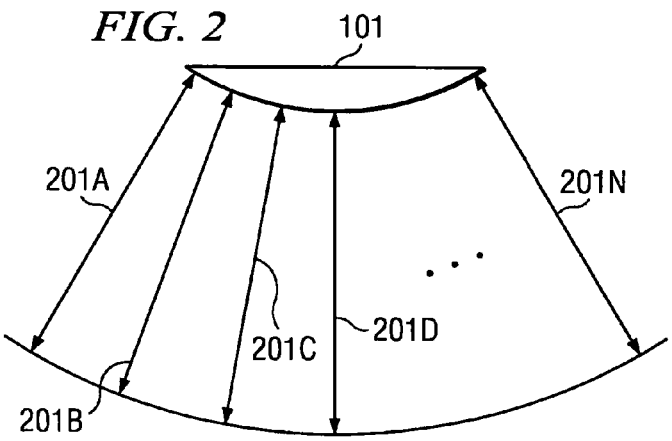
FIG. 2 shows acoustic signal lines forming a frame for ultrasonic image forming.

FIG. 2 illustrates operation of system 100 in obtaining an ultrasonic image. The elements of transducer 101 are excited using controlled phase and amplitude relationships in order to produce beams of acoustic signals transmitted from transducer 101 as well as beams for receiving reflected acoustic signals. Specifically, the elements of transducer 101 are energized to transmit and receive an acoustic pulse along each of acoustic signal scan lines 201A-201N. Acoustic echo information from each of lines 201A-201N is processed and combined (such as using receiver/transmitter module 102, beamformer module 103, DSP module 104, and back end module 105 of FIG. 1) to form an ultrasonic image (as may be displayed by display 106 of FIG. 1). Accordingly, lines 201A-201N comprise an acoustic signal scan frame.

It should be appreciated that upon acquisition of an acoustic signal, scan line processing may be performed by components of system 100 before acquisition of a subsequent acoustic signal scan line. For example, DSP 104 may provide filtering or smoothing operations with respect to the information of an acoustic signal scan line in order to improve the quality of an image formed therefrom. Additionally or alternatively, DSP 104 may provide mode specific processing, such as to provide color Doppler or three-dimensional processing. Similarly, back end module 105 may provide scan control operation, such as determining beam forming weighting for a subsequent scan line, during the time between scan lines. The foregoing processing performed between each successive acoustic signal scan line acquisition operation may result in appreciable acoustic signal "dead" time with respect to particular acoustic signal path circuitry. For example, each of transducer 101, receive/transmit module 102, and beamformer module 103 may be substantially idle with respect to acoustic signal processing after acoustic signal acquisition before a subsequent acoustic signal acquisition cycle. Likewise, DSP module 104 may be idle with respect to acoustic signal processing for an appreciable amount of time after acoustic acquisition before a subsequent acoustic signal acquisition cycle.

Similar to acoustic signal scan line acquisition discussed above, components of system 100 in the acoustic signal path may experience acoustic signal dead time between acoustic signal frames due to processing being performed by components of system 100 before acquisition of a subsequent acoustic signal frame. For example, back end module 105 may provide image processing, such as scan line aggregation, grayscale mapping, etcetera, as well as scan control operations, such as determining beam forming weighting for a subsequent scan line, during the time between frames. The foregoing processing performed between each successive acoustic signal scan frame may result in appreciable acoustic signal dead time with respect to particular acoustic signal path circuitry.

Embodiments of the present invention operate to power-down select components of system 100 during the aforementioned acoustic signal dead time between scan lines and/or scan frames and to power-up those components prior to their being used in a next acoustic signal acquire cycle. For example, controller 110, such as may comprise a central processing unit (CPU) having attendant memory and input/output (I/O) interfaces and operable under control of an instruction set defining operation as described herein, may operate to determine an acoustic signal dead time (whether associated with scan lines, scan frames, or other epoch) and control one or more of transducer 101, receive/transmit module 102, beamformer module 103, and DSP module 104 to power-down and power-up at appropriate times. Through proper scheduling of the aforementioned power-down and power-up cycles, energy of battery 120 may be conserved without undesirably affecting operation of system 100 as perceived by a user thereof.

Figure 3:
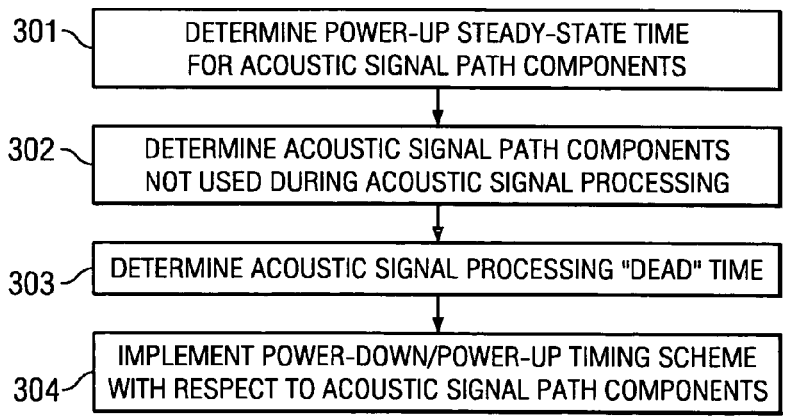
FIG. 3 a flow diagram of operation of the system of FIG. 1 in providing power-down and power-up cycles according to an embodiment of the invention.

Directing attention to FIG. 3, a flow diagram of operation of controller 120 in providing power-down and power-up cycles according to an embodiment of the invention is shown. At block 301 controller 120 determines a time for one or more of transducer 101, receive/transmit module 102, beamformer module 103, and DSP module 104 and/or circuitry thereof to reach steady-state operation after power-up. For example, controller 120 may monitor operation of each of the foregoing during a power-up procedure to determine their operating characteristics. Additionally or alternatively, a memory may be programmed with the foregoing information, such as during a calibration step prior to system 100 being released to the field.

At block 302 controller 120 determines particular ones of transducer 101, receive/transmit module 102, beamformer module 103, and DSP module 104 which are idle during acoustic signal processing following acoustic signal scan line acquisition and/or acquisition of a scan frame. For example, controller 120 may monitor operation of each of the foregoing during signal processing to determine their operational state. Determinations as made at block 302 may include information in addition to whether or not particular components are idle during acoustic signal processing following acquisition. For example, controller 120 may determine how long after an acoustic signal acquisition cycle components become idle, such as to accommodate powering-down a component that provides some post acoustic signal acquisition processing. Similarly, controller 120 may determine how long before a subsequent acoustic signal acquisition cycle components cease to be idle, such as to accommodate powering-down and properly powering-up a component that provides some pre acoustic signal acquisition processing. It should be appreciated that the foregoing information may differ depending upon a particular operating mode system 100 is operating in. Accordingly, such determinations may be made with respect to a plurality of operating modes or other conditions. Additionally or alternatively, a memory may be programmed with the foregoing information, such as during a calibration step prior to system 100 being released to the field.

At block 303 controller 120 determines an acoustic signal processing dead time associated with acoustic signal processing between scan line and/or scan frame acquire cycles. It should be appreciated that the foregoing information may differ depending upon a particular operating mode system 100 is operating in. Accordingly, such determinations may be made with respect to a plurality of operating modes or other conditions. Additionally or alternatively, a memory may be programmed with the foregoing information, such as during a calibration step prior to system 100 being released to the field.

At block 304 controller 120 implements a power-down and power-up timing scheme with respect to one or more of transducer 101, receive/transmit module 102, beamformer module 103, and DSP module 104. Through operation of the foregoing power-down and power-up timing scheme, controller 120 of an embodiment provides control signals such that power is reduced to particular circuits (or portions thereof) and/or particular circuits (or portions thereof) are deactivated during acoustic signal processing after an acoustic signal acquire cycle and are powered-up or reactivated in sufficient time to reach steady-state operation prior to their use in a subsequent acoustic signal acquisition cycle.

Implementing a method as set forth in FIG. 3, embodiments of the present invention operate to power-down particular acoustic signal path circuitry during acoustic signal dead time between acoustic signal line acquisition. In operation according to an embodiment, as a previous acoustic signal line is being processed and circuitry is being configured for a next acoustic signal line acquisition, transmit amplifiers, receive buffers, and transmit/receive switches of receive/transmit module 102 are powered-down, A/D converters, filters, and beam formers of beamformer module 103, and DSPs of DSP module 104 are powered-down according to the present invention. These circuits are preferably powered-up a sufficient time before a next acoustic signal acquisition cycle to facilitate their use therein without impacting performance of system 100.

Additionally or alternatively, embodiments of the present invention implementing a method as set forth in FIG. 3 operate to power-down particular acoustic signal path circuitry during acoustic signal dead time between acoustic signal frames. In the time between when a last acoustic signal line has been acquired for a previous frame and a first acoustic signal line is to be acquired for a next frame, transmit amplifiers, receive buffers, and transmit/receive switches of receive/transmit module 102, A/D converters and filters of beamformer module 103, and DSPs of DSP module 104, are powered-down according to an embodiment. These circuits are preferably powered-up a sufficient time before a next acoustic signal acquisition cycle (e.g., the beginning of a next frame) to facilitate their use therein without impacting performance of system 100.

It should be appreciated that the above described power-down and power-up cycles provide appreciable power savings with no performance cost according to embodiments of the invention. Specifically, because circuits which are idle during particular signal processing phases are powered-down and then powered-up again prior to their being needed, image quality and signal processing speed remains unaffected according to such embodiments. Moreover, circuits such as transmit amplifiers, A/D converters, and DSPs often account for considerable amounts of consumed energy, thus resulting in appreciable energy conservation through use of the above described power-down and power-up cycles, although such cycles may be relatively short (particularly in the case of inter-line cycles).

As circuitry which is utilized in signal processing and display remains active according to embodiments of the invention, a user may remain ignorant with respect to the operation of the power-down cycles and may continue to interact with system 100 as if no power-down cycles have been invoked. Accordingly, all features and functions that are available to a user in normal operation of system 100 may continue to be available to such a user when embodiments of the present invention are active to conserve power.

The circuitry which is powered-down between lines and the circuitry which is powered-down between frames may not be the same according to embodiments of the invention. For example, the acoustic signal dead time between acoustic signal frames may be greater than the acoustic signal dead time between acoustic signal lines, allowing circuitry which requires a relatively long power-up steady state time to be powered-down and powered-up again between frames whereas such circuitry may not be powered-down and powered-up again between lines without impacting system operation. Additionally or alternatively, the circuitry which is idle during the acoustic signal dead time between acoustic signal frames and the circuitry which is idle during the acoustic signal dead time between acoustic signal lines may not be the same. Accordingly, circuitry powered-down between acoustic signal frames according to embodiments of the present invention may include circuitry, in addition to or in the alternative to the circuitry powered-down between acoustic signal lines.

In order to further conserve power, embodiments of the present invention operate to adjust the acoustic signal dead time circuitry power-down cycle, such as by adjusting acoustic signal frame rates. For example, by controller 110 determining a particular scan mode that the portable ultrasonic diagnostic system has been placed in, the acoustic signal frame rate may be adjusted to provide an optimized acoustic signal dead time circuitry power-down cycle. Specifically, by selecting a longer frame rate, controller 110 may control the acoustic signal dead time to facilitate increased power conservation. According to embodiments of the invention, a frame rate is selected which provides an acoustic signal dead time sufficient to facilitate the powering-down of additional circuitry, such as circuitry which otherwise has a power-up steady-state time too long for powering-down during acoustic signal dead time without affecting system operation.

The foregoing acoustic signal dead time adjustment techniques may be implemented in a variety of scenarios according to embodiments of the invention. For example, controller 110 may operate to provide an increased acoustic signal dead time, and thus an increased power-down period with respect to circuitry of system 100, when it is determined that active ultrasonic scanning is not currently taking place. After determining that the scanned image remains substantially unchanged, controller 110 may adjust the acoustic signal frame rate to provide an increased acoustic signal dead time and a longer circuitry power-down cycle, thereby reducing power consumption. Controller 110 may determine that an image remains unchanged by comparing image information available from back end module 105 associated with successive frames and which a predetermined number of frames show less than a threshold amount of change (e.g., less than 10% of the pixels are changed), it may be determined that transducer 101 is not currently being actively used for image scanning. The foregoing decreased frame rate may be implemented to provide power conservation according to embodiments of the invention without compromising image quality because the successive images remain unchanged. In operation according to preferred embodiments, the frame rate is again increased to its original rate when the scanned image is changed.

Embodiments of the present invention implement the foregoing power-down techniques in various combinations, including combinations of the foregoing techniques as well as combinations of one or more of the foregoing techniques with other power management techniques. Accordingly, power-down cycles may be implemented between acoustic signal lines and/or acoustic signal frames and additional power management techniques may be implemented. For example, portable ultrasound diagnostic system circuitry not necessary for a currently selected mode of operation may be powered-down throughout operation of that mode in addition to implementing acoustic signal dead time power-down cycles with respect to other circuitry. According to embodiments of the invention, beamformer module 103 includes multiple beam forming circuits, such as an analog beam former useful with respect to continuous wave (CW) modes of operation and a digital beam former useful with respect to pulsed wave (PW) modes of operation. When a CW mode is selected with respect to system 100, controller 110 may cause that portion of beamformer module 103 associated with the digital beam former to be powered-down in addition to implementing acoustic signal dead time power-down cycles as described above. Likewise, when a PW mode is selected with respect to system 100, controller 110 may cause that portion of beamformer module 103 associated with the analog beam former to be powered-down in addition to implementing acoustic signal dead time power-down cycles.

Similar to the mode driven power conservation techniques discussed above, embodiments of the invention may implement power conservation techniques associated with accessories or components currently selected or utilized. For example, where system 100 includes a plurality of transducers (not shown), such as a transducer for superficial abdominal use and a transducer for intraoperative vascular use, which may employ different circuitry of system 100. Accordingly, in addition to power-down cycles being implemented between acoustic signal lines and/or acoustic signal frames and an additional power management technique may be implemented wherein circuitry of system 100 not necessary for a currently selected one of the transducers may be powered-down throughout its use.

Application of the foregoing power-down techniques of the present invention is not limited to addressing power issues. Embodiments of the present invention may be utilized in controlling thermal aspects of the operation of a portable ultrasound diagnostic system. For example, portable ultrasonic diagnostic systems such as those shown and described in the above referenced patent application entitled "ULTRASONIC TRANSDUCER HAVING A THIN WIRE INTERFACE," and "PROCESSING OF MEDICAL SIGNALS," provide a density of the electronics therein such that increased operating temperatures may be experienced with respect to one or more components. In particular, placing of system components, such as receive/transmit module 102, beamformer module 103, and/or DSP module 104 within a transducer housing may present challenges with respect to heat dissipation, although providing other advantages as described in the above referenced patent application.

Embodiments of the present invention implement the foregoing acoustic signal dead time power-down cycles to decrease the thermal output of circuitry of system 100, without undesirably affecting operation thereof. Accordingly, in addition to conserving power, such embodiments of the invention may ensure that excess thermal energy which might not be sufficiently dissipated is not created.

Moreover, embodiments of the present invention utilize one or more thermal detectors (not shown) coupled to controller 110 in order to determine if excess thermal energy is present and, thus, that power-down cycles of the present invention should be invoked. For example, a thermister may be disposed in transducer 101 and, if an excessive thermal condition is detected, the foregoing technique of adjusting the acoustic signal dead time circuitry power-down cycle may be invoked in order to allow thermal energy to dissipate. Such a technique may result in other than desired performance by the portable ultrasonic diagnostic system during such times, however such decreased performance is offset by the continued ability for the system to operate.

Although the above exemplary embodiments have been primarily discussed with reference to providing power conservation by powering-down circuits without affecting system operation, it should be appreciated that the techniques may be implemented in scenarios which affect system operation, if desired. It is generally preferred that power conservation not impede system performance, whether in processing speed, output quality, or information level. However, there may be situations where one or more aspects of system operation are advantageously sacrificed for power conservation. For example, continued operation of the system at some nominal level may be desired over accelerated failure of the device. According to one embodiment, controller 110 monitors a reserve capacity of battery 120 and when the reserve falls below a predetermined threshold, begins implementing power-down and power-up timing schemes which maximize power conservation, although performance of system 100 may be affected. For example, controller 110 may power-down components during scan line acoustic signal dead times which have a power-up steady-state time which otherwise suggests those components should not be powered-down. Likewise, controller 110 may delay or schedule component power-up, such as to power-up components in an order which taxes the battery the least, although components may not be powered-up in time to perform their processes without delaying system operation.

Although the present invention and its advantages have been described in detail, it should be understood that various changes, substitutions and alterations can be made herein without departing from the invention as defined by the appended claims. Moreover, the scope of the present application is not intended to be limited to the particular embodiments of the process, machine, manufacture, composition of matter, means, methods and steps described in the specification. As one will readily appreciate from the disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps.

What is claimed is:

1. A method for providing power management in an ultrasound system, said method comprising:
   determining acoustic signal processing dead time;
   implementing a power-down and power-up timing scheme with respect to particular circuitry disposed in an acoustic signal processing path during said acoustic signal processing dead time without affecting a user's perception of operation of said ultrasound system;
   controlling the duration of said acoustic signal processing dead time to provide an extended power-down period with respect to said particular circuitry;
   determining a scanned image change status, wherein said controlling the duration of said acoustic signal processing dead time is provided when said scanned image change status indicates a scanned image remains unchanged; and
   controlling the duration of said intra scan frame period to provide a reduced power-down period with respect to said particular circuitry when said scanned image change status indicates said scanned image is changed.

2. The method of claim 1, wherein said acoustic signal processing dead time corresponds to an intra scan line period.

3. The method of claim 1, wherein said acoustic signal processing dead time corresponds to a period between groups of scan lines.

4. The method of claim 1, wherein said acoustic signal processing dead time corresponds to an intra scan frame period.

5. The method of claim 1, further comprising:
determining a thermal aspect of a component of said ultrasound system, wherein said controlling the duration of said acoustic signal processing dead time to decrease said thermal aspect.

6. The method of claim 5, wherein said component comprises a transducer assembly and said thermal aspect comprises a temperature exceeding a predetermined threshold.

7. The method of claim 1, further comprising:
determining an acoustic signal processing dead time facilitating said particular circuitry including a number of circuits optimizing power consumption with respect to said ultrasound system.

8. The method of claim 1, wherein said particular circuitry comprises circuitry which is not used during acoustic signal processing.

9. The method of claim 8, wherein said particular circuitry comprises circuitry which is used during acoustic signal acquisition.

10. The method of claim 8, wherein said particular circuitry further comprises circuitry having a power-up steady-state time determined to be of a duration facilitating powering-down and powering-up said particular circuitry during said acoustic signal processing dead time.

11. The method of claim 8, wherein said particular circuitry comprises transducer circuitry.

12. The method of claim 8, wherein said particular circuitry comprises transmit amplifier circuitry.

13. The method of claim 8, wherein said particular circuitry comprises receive buffer circuitry.

14. The method of claim 8, wherein said particular circuitry comprises analog to digital converter circuitry.

15. The method of claim 8, wherein said particular circuitry comprises filter circuitry.

16. The method of claim 8, wherein said particular circuitry comprises beamformer circuitry.

17. The method of claim 8, wherein said particular circuitry comprises digital signal processor circuitry.

18. An ultrasound instrument power management system, said system comprising:
a controller coupled to acoustic signal acquisition circuitry, at least a portion of said acoustic signal acquisition circuitry remaining idle during an idle time after acoustic signal acquisition and during subsequent ultrasound instrument signal processing, wherein said controller includes an instruction set defining operation to implement a power-down and power-up timing scheme with respect to said at least a portion of said acoustic signal acquisition circuitry during said idle time, wherein said controller includes a memory storing information with respect to a power-up steady-state time associated with circuitry of said acoustic signal acquisition circuitry, wherein said instruction set determines said at least a portion of said acoustic signal acquisition circuitry for implementing said power-down and power-up timing scheme through reference to said information with respect to said power-up steady-state time.

19. The system of claim 18, wherein said instruction set implements a different power-down and power-up timing scheme with respect to an idle time associated with an inter scan line period and an idle time associated with an inter scan frame period.

20. The system of claim 19, wherein said at least a portion of said acoustic signal acquisition circuitry for which said power-down and power-up timing scheme is implemented is different with respect an idle time associated with an inter scan line period and an idle time associated with an inter scan frame period.

21. The system of claim 18, wherein said controller provides adjustment of said idle time under control of said instruction set.

22. The system of claim 21, wherein said adjustment of said idle time lengthens said idle time to facilitate addition of acoustic signal acquisition circuitry to said at least a portion of said acoustic signal acquisition circuitry.

23. The system of claim 21, wherein said adjustment of said idle time lengthens said idle time to facilitate heat dissipation with respect to said at least a portion of said acoustic signal acquisition circuitry.

24. The system of claim 23, wherein said controller is further coupled to a thermal sensor, said thermal sensor providing information utilized in said adjustment of said idle time.

25. The system of claim 18, wherein said at least a portion of said acoustic signal acquisition circuitry comprises a transducer.

26. The system of claim 18, wherein said at least a portion of said acoustic signal acquisition circuitry comprises a transmission amplifier.

27. The system of claim 18, wherein said at least a portion of said acoustic signal acquisition circuitry comprises a receive buffer.

28. The system of claim 18, wherein said at least a portion of said acoustic signal acquisition circuitry comprises an analog to digital converter.

29. The system of claim 18, wherein said at least a portion of said acoustic signal acquisition circuitry comprises a filter.

30. The system of claim 18, wherein said at least a portion of said acoustic signal acquisition circuitry comprises a beam former.

31. The system of claim 18, wherein said at least a portion of said acoustic signal acquisition circuitry comprises a digital signal processor.

32. The system of claim 18, wherein said at least a portion of said acoustic signal acquisition circuitry comprises a receive and transmit application specific integrated circuit.

33. The system of claim 18, wherein said at least a portion of said acoustic signal acquisition circuitry comprises a beamformer application specific integrated circuit.

34. The system of claim 18, wherein said at least a portion of said acoustic signal acquisition circuitry comprises a digital signal processor application specific integrated circuit.

35. The system of claim 18, wherein said controller comprises an application specific integrated circuit.

36. The system of claim 18, wherein said ultrasound instrument comprises a portable ultrasound diagnostic instrument.

37. A portable ultrasound system power management method comprising:
determining a power-up steady-state time for acoustic signal path components of said portable ultrasound system;
determining one or more acoustic signal path components of said acoustic signal path components not used during acoustic signal processing subsequent to acoustic signal acquisition;

determining an acoustic signal processing dead time associated with said acoustic signal processing subsequent to acoustic signal acquisition; and implementing a power-down and power-up timing scheme with respect to at least a portion of said one or more acoustic signal path components during said dead time, said at least a portion of said one or more acoustic signal path components having a power-up steady-state time facilitating said power-down and power-up timing scheme without degrading operation of said portable ultrasound system.

38. The method of claim 37, further comprising:
controlling said dead time to facilitate inclusion of additional acoustic signal path components in said at least a portion of said one or more acoustic signal path components.

39. The method of claim 37, further comprising:
controlling said dead time to facilitate heat dissipation with respect to said one or more acoustic signal path components.

40. The method of claim 37, further comprising:
determining when active scanning is not occurring with respect to said portable ultrasound; and
controlling said dead time to reduce power utilization by said portable ultrasound when said active scanning is not occurring.

41. The method of claim 40, wherein said determining when active scanning is not occurring comprises:
determining if an image processed by said portable ultrasound is changing.

42. The method of claim 37, wherein said dead time corresponds to an inter scan line processing time.

43. The method of claim 37, wherein said dead time corresponds to an inter scan frame processing time.

44. The method of claim 37, further comprising:
processing signals normally by other components of said portable ultrasound during implementation of said power-down and power-up timing scheme.

45. An ultrasound instrument power management system, said system comprising:
a controller coupled to acoustic signal acquisition circuitry, at least a portion of said acoustic signal acquisition circuitry remaining idle during an idle time after acoustic signal acquisition and during subsequent ultrasound instrument signal processing, wherein said controller includes an instruction set defining operation to implement a power-down and power-up timing scheme with respect to said at least a portion of said acoustic signal acquisition circuitry during said idle time, wherein said instruction set implements a different power-down and power-up timing scheme with respect to an idle time associated with an inter scan line period and an idle time associated with an inter scan frame period.

46. The system of claim 45 wherein said controller includes a memory storing information with respect to a power-up steady-state time associated with circuitry of said acoustic signal acquisition circuitry, wherein said instruction set determines said at least a portion of said acoustic signal acquisition circuitry for implementing said power-down and power-up timing scheme through reference to said information with respect to said power-up steady-state time.

47. The system of claim 45, wherein said at least a portion of said acoustic signal acquisition circuitry for which said power-down and power-up timing scheme is implemented is different with respect an idle time associated with an inter scan line period and an idle time associated with an inter scan frame period.

48. The system of claim 45, wherein said controller provides adjustment of said idle time under control of said instruction set.

49. The system of claim 48, wherein said adjustment of said idle time lengthens said idle time to facilitate addition of acoustic signal acquisition circuitry to said at least a portion of said acoustic signal acquisition circuitry.

50. The system of claim 48, wherein said adjustment of said idle time lengthens said idle time to facilitate heat dissipation with respect to said at least a portion of said acoustic signal acquisition circuitry.

51. The system of claim 50, wherein said controller is further coupled to a thermal sensor, said thermal sensor providing information utilized in said adjustment of said idle time.

52. The system of claim 45, wherein said at least a portion of said acoustic signal acquisition circuitry comprises a transducer.

53. The system of claim 45, wherein said at least a portion of said acoustic signal acquisition circuitry comprises a transmission amplifier.

54. The system of claim 45, wherein said at least a portion of said acoustic signal acquisition circuitry comprises a receive buffer.

55. The system of claim 45, wherein said at least a portion of said acoustic signal acquisition circuitry comprises an analog to digital converter.

56. The system of claim 45, wherein said at least a portion of said acoustic signal acquisition circuitry comprises a filter.

57. The system of claim 45, wherein said at least a portion of said acoustic signal acquisition circuitry comprises a beam former.

58. The system of claim 45, wherein said at least a portion of said acoustic signal acquisition circuitry comprises a digital signal processor.

59. The system of claim 45, wherein said at least a portion of said acoustic signal acquisition circuitry comprises a receive and transmit application specific integrated circuit.

60. The system of claim 45, wherein said at least a portion of said acoustic signal acquisition circuitry comprises a beamformer application specific integrated circuit.

61. The system of claim 45, wherein said at least a portion of said acoustic signal acquisition circuitry comprises a digital signal processor application specific integrated circuit.

62. The system of claim 45, wherein said controller comprises an application specific integrated circuit.

63. The system of claim 45, wherein said ultrasound instrument comprises a portable ultrasound diagnostic instrument.

* * * * *